United States Patent [19]

Knaus et al.

[11] 4,338,445
[45] Jul. 6, 1982

[54] N-(CARBONYLAMINO)-TETRAHYDROPYRIDYL DERIVATIVES

[75] Inventors: Edward E. Knaus; Linda A. Corleto, both of Edmonton, Canada; Kinfe Redda, San Juan, P.R.

[73] Assignee: Canadian Patents & Development Limited, Ottawa, Canada

[21] Appl. No.: 179,249

[22] Filed: Aug. 18, 1980

[30] Foreign Application Priority Data

Aug. 31, 1979 [CA] Canada .................................. 335090

[51] Int. Cl.$^3$ ............................................ C07D 213/89
[52] U.S. Cl. .................................... 546/270; 546/300; 546/311; 546/316; 546/318; 546/322
[58] Field of Search ............... 546/311, 316, 322, 318, 546/300, 270

[56] References Cited

U.S. PATENT DOCUMENTS 4,088,653 5/1978 Knaus et al. ..................... 546/309

OTHER PUBLICATIONS

Burger, Medicinal Chemistry, Second Edition, p. 43, Interscience Pub., 1960.

Primary Examiner—Alan L. Rotman
Attorney, Agent, or Firm—Alan A. Thomson

[57] ABSTRACT

Pharmaceutical compounds of the general formula

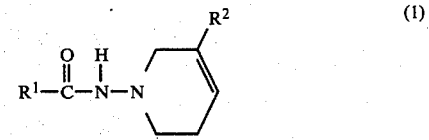

and non-toxic pharmaceutically-acceptable salts thereof wherein
  $R^1$ is inter alia alkyl, cycloalkyl, aralkyl, or certain pyridyl or phenyl radicals, and with proviso
  $R^2$ is selected from hydrogen, lower alkyl, lower alkoxy, amino, hydroxyl, halogen, carboxyl, amido, and —CON(lower alkyl)$_2$. Methods of preparing these compounds are described. The compounds exhibit analgesic, anti-inflammatory, hyperglycemic and/or hypoglycemic activity.

9 Claims, No Drawings

N-(CARBONYLAMINO)-TETRAHYDROPYRIDYL DERIVATIVES

The present invention relates to pharmaceutical compounds. More particularly, the invention relates to N-(carbonylamino)-1,2,3,6-tetrahydropyridyl derivatives or non-toxic pharmaceutically-acceptable salts thereof having particular physiological effects. This invention also relates to a process for preparing the above compounds and to methods for their use.

The novel N-(carbonylamino)-1,2,3,6-tetrahydropyridyl derivatives of the present invention are represented by the structural formula (1):

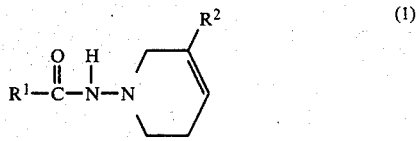

wherein $R^1$ is selected from alkyl having from 1-24 carbon atoms, cycloalkyl having 3-7 carbon atoms, aralkyl having 1-6 carbon atoms in the alkyl group, phenoxyalkyl having 1-6 carbon atoms in the alkyl group, pyridylalkyl having 1-6 carbon atoms in the alkyl group, N-(lower alkoxy)carbonyl-1,2-dihydropyridyl, N-(lower alkoxy)carbonyl-1,2,3,6-tetrahydropyridyl, N-(lower alkyl)-1,2,3,6-tetrahydro-pyridyl, pyridyl-1-oxide, and optionally-substituted pyridyl or phenyl represented by the formula (2)

in which $R^4$ and $R^5$ are the same or different and each represents hydrogen, lower alkyl, lower alkoxy, $NH_2$, OH, halogen, COOH, $CONH_2$, or CON(lower alkyl)$_2$; and $R^2$ is selected from hydrogen, lower alkyl, lower alkoxy, $NH_2$, OH, halogen, COOH, $CONH_2$, and CON(lower alkyl)$_2$, with the proviso that when $R^4$ and $R^5$ are both hydrogen, or when $R^4$ is hydrogen and $R^5$ is lower alkyl or lower alkoxy, then $R^2$ is other than hydrogen, lower alkyl or lower alkoxy; and the non-toxic pharmaceutically-acceptable salts of the compounds defined above. The term "lower" denotes the presence of 1-4 carbon atoms in a straight or branched chain. The compounds possess analgesic, anti-inflammatory, hyperglycemic, and/or hypoglycemic activities.

BACKGROUND OF THE INVENTION

Related derivatives of 1,2,3,6-tetrahydropyridine have been described by Knaus et al, in J. Het. Chem. 13, 1237 (1976) and in U.S. Pat. No. 4,088,653 issued May 9, 1978 (which corresponds to Knaus et al., Canadian Patent Application No. 283,573 filed July 27, 1977).

SUMMARY DESCRIPTION OF THE INVENTION

The desired N-(carbonylamino)-1,2,3,6-tetrahydropyridyl derivatives are prepared by reacting a carbonyl hydrazide of the formula (3)

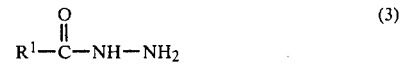

wherein $R^1$ is as defined above except that it may not be N-(lower alkyl)-1,2,3,6-tetrahydropyridyl or N-(lower alkoxy)carbonyl-1,2-dihydro- or -1,2,3,6-tetrahydropyridyl group, with an arylpyridinium halide of structural formula (4)

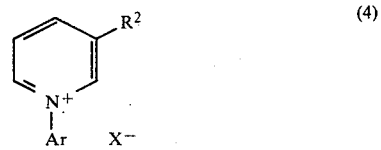

wherein $R^2$ is selected from the group consisting of lower alkyl, amido, amino, carboxyl, lower dialkylaminocarbonyl, halogeno, hydrogen, and hydroxyl, Ar represents an aryl or substituted aryl group, and X is Cl, Br or I, heating the product sufficiently to convert to N-(carbonyliminopyridinium) ylide of the formula (5)

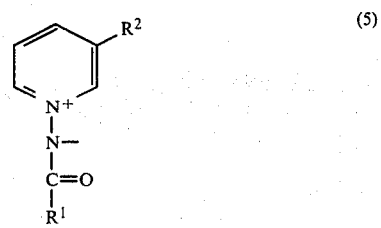

wherein $R^1$ and $R^2$ are as defined above, and converting this pyridinium ylide in the presence of a suitable reducing agent to a corresponding N-(carbonylamino)-1,2,3,6-tetrahydropyridyl derivative.

These N-(carbonylamino)-1,2,3,6-tetrahydropyridyl derivatives wherein $R^2$ is as defined above and $R^1$ is a N-lower alkyl-1,2,3,6-tetrahydropyridyl,N-lower alkoxycarbonyl-1,2,3,6-tetrahydropyridyl or N-lower alkoxycarbonyl-1,2-dihydropyridyl substituent are prepared by reacting a N-(pyridylcarbonylamino)-1,2,3,6-tetrahydropyridine of the formula (1) in which $R^1$ is pyridyl and $R^2$ is as defined above, with a lower alkyl halide or lower alkoxy carbonyl halide and stirring sufficiently to convert to the corresponding N-(lower alkyl or lower alkoxy carbonyl) pyridinium salt of the formula (6)

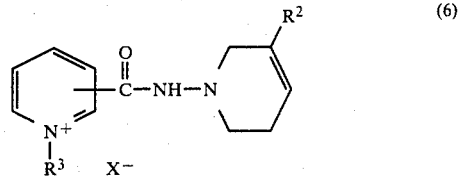

wherein $R^2$ is as defined above and $R^3$ is a lower alkyl or lower alkoxycarbonyl substituent, and X is Cl, Br or I, and converting this pyridinium salt in the presence of a suitable reducing agent to the corresponding N-(lower alkyl-1,2,3,6-tetrahydropyridyl, N-lower alkoxycarbonyl-1,2,3,6-tetrahydropyridyl or N-lower alkoxycarbonyl-1,2-dihydropyridyl derivative.

DETAILED DESCRIPTION OF THE INVENTION

The starting materials for the preparation of the compounds of formula (1), viz., the carbonyl hydrazides of formula (3) and the arylpyridinium halides of formula (4) are either known or are conveniently prepared from known starting materials by methods known per se. It has been found that the 2,4-dinitrophenyl group is particularly advantageous as the aryl or substituted aryl group in the arylpyridinium halides of formula (4), and that the reaction between the starting materials of formulae (3) and (4) is conveniently carried out in a solvent in which both compounds (3) and (4) are soluble, e.g. a lower alkanol such as methanol or ethanol, initially at temperatures within the range of from $-10°$ C. to $10°$ C., preferably at about $0°$ C., followed by warming to $15°-45°$ C., preferably to ambient temperature, in the presence of a base, preferably an organic base such as a tri(lower alkyl)amine, e.g. triethylamine. The resulting solid is separated, suspended in a mixture of water and a water-miscible organic solvent such as a cyclic ether, e.g. dioxane or tetrahydrofuran, and the reaction is completed by heating to about $50°-100°$ C. for 2-24 hours, preferably to the reflux temperature of the mixture for 12 hours, to obtain the corresponding ylide of formula (5) which may be purified, e.g. by chromatography. Said ylide (5) is then treated with a suitable reducing agent, preferably an alkali metal borohydride such as sodium borohydride or sodium cyanoborohydride, at temperatures within the range of $-10°$ C. to $10°$ C., preferably at about $0°$ C., followed by warming to ambient temperature. The duration of that latter reaction may be from 2-8 hours, preferably for 4-5 hours. Dilution with ice, extraction with a water-immiscible solvent such as a halogenated hydrocarbon, e.g. methylene dichloride, ethylene dichloride, chloroform, or carbon tetrachloride, and evaporation of the solvent gives the corresponding compound of formula (1).

When it is desired to obtain compounds of formula (1) in which $R^2$ is as defined in the first instance and $R^1$ is N-(lower alkyl)- or N-(lower alkoxy)carbonyl-1,2,3,6-tetrahydropyridyl or N-(lower alkoxy)carbonyl-1,2-dihydropyridyl, the corresponding compound of formula (1) in which $R^2$ is as defined above and $R^1$ is pyridyl, is treated with a lower alkyl halide, e.g. methyl iodide, or with a lower alkoxycarbonyl halide, e.g. methyl chloroformate, in an inert solvent such as a lower alkanol, e.g. methanol or ethanol, or in a halogenated hydrocarbon such as methylene dichloride or chloroform, at a temperature within the range of from $-50°$ C. to $-95°$ C., preferably at about $-65°$ C., for 10-60 minutes, preferably for about 30 minutes, to obtain the corresponding pyridinium salt of formula (6) in which $R^2$ is as defined above, $R^3$ is lower alkyl or lower alkoxycarbonyl, respectively, and X is the ion of the halogen present in the alkyl or alkoxycarbonyl halide. A suitable reducing agent such as an alkali metal borohydride, preferably sodium borohydride, is added and the reduction is allowed to proceed under varying conditions depending upon the nature of the final product which is desired. Other equivalent reducing agents can be selected. Thus, when it is desired to obtain a compound of formula (1) in which $R^2$ is as defined above and $R^1$ is N-(lower alkoxy)carbonyl-1,2-dihydropyridyl or N-(lower alkyl)-1,2,3,6-tetrahydro-pyridyl, the reduction is carried out at $-50°$ C. to $-95°$ C., preferably at about $-65°$ C., for 2-6 hours, preferably for about 3 hours. When it is desired to obtain a compound of formula (1) in which $R^2$ is as defined above and $R^1$ is N-(lower alkoxy)carbonyl-1,2,3,6-tetrahydropyridyl the reduction is carried out at $-10°$ C. to $10°$ C., preferably at about $0°$ C., for 2-6 hours, preferably for about 4 hours. The work-up in all the above procedures comprises dilution with ice, extraction with a water-immiscible solvent such as a halogenated hydrocarbon, e.g. methylene dichloride, chloroform, or carbon tetrachloride; and evaporation of the solvent gives the corresponding compound of formula (1) which may be purified, e.g. by chromatography.

More particularly, the following compounds have been prepared, and through testing, have been found to have the following physiological activity:

| Name | Designation | Physiological Activity |
| --- | --- | --- |
| N-(2-pyridylcarbonylamino-1-oxide)-1,2,3,6-tetrahydropyridine | A-36 | analgesic, anti-inflammatory |
| N-(benzoylamino)-3(diethylaminocarbonyl)-1,2,3,6-tetrahydropyridine | A-43 | analgesic |
| N-[4-(1-methoxycarbonyl-1,2-dihydropyridyl)carbonylamino]-1,2,3,6-tetrahydropyridine | A-45 | analgesic, anti-inflammatory |
| N-(3-picolylcarbonylamino)-1,2,3,6-tetrahydropyridine | A-48 | analgesic, anti-inflammatory |
| N-[4-(1-methoxycarbonyl-1,2,3,6-tetrahydropyridyl)carbonylamino]-1,2,3,6-tetrahydropyridine | A-49 | analgesic, anti-inflammatory |
| N-[4-(1-methyl-1,2,3,6-tetrahydropyridyl)carbonylamino]-1,2,3,6-tetrahydropyridine | A-50 | analgesic |
| N-(phenylethylcarbonylamino)-1,2,3,6-tetrahydropyridine | A-55 | analgesic, anti-inflammatory |
| N-(phenoxymethylenecarbonylamino)-1,2,3,6-tetrahydropyridine | A-62 | analgesic, anti-inflammatory, hypergylcemic |
| N-(cyclohexylcarbonylamino)-1,2,3,6-tetrahydropyridine | A-63 | analgesic, anti-inflammatory, hyperglycemic |
| N-(3,4-methylenedioxyphenylmethylenecarbonylamino)-1,2,3,6-tetrahydropyridine | A-70 | analgesic |
| N-(4-methoxyphenylcarbonylamino)-1,2,3,6-tetrahydropyridine | A-77 | analgesic, hypoglycemic |
| N-(4-methylphenylcarbonylamino)-1,2,3,6-tetrahydropyridine | A-78 | analgesic, hypoglycemic |
| N-(4-chlorophenylcarbonylamino)-1,2,3,6-tetrahydropyridine | A-79 | analgesic, hypoglycemic |
| N-(3,4-dichlorophenylcarbonylamino)- | | |

| Name | Designation | Physiological Activity |
| --- | --- | --- |
| 1,2,3,6-tetrahydropyridine | A-80 | analgesic, hypoglycemic |

Suitable pharmaceutically-acceptable salt forms of these compounds include alkaline metal salts, for example the potassium or sodium salt, and the ammonium salt, and alkaline earth metal salts, e.g. the calcium salt, as well as the mineral acid salts, for example, the hydrochloride and hydrobromide salts.

The compounds of formula (1) have anti-inflammatory, analgesic, hyperglycemic, and/or hypoglycemic properties. The anti-inflammatory activities are demonstrated in the rat in a modification of the test using the carrageenan-induced paw edema described by C. A. Winter, p.190–202, Int. Symposium on Non-Steroidal Anti-Inflammatory Drugs, Milan, 1964, Excerpta Medica Foundation, Amsterdam. The analgesic properties are demonstrated in a modification of the phenylquinone-induced muscular writhing test in mice described by Collier et al, in Brit. J. Pharmac. Chemother. 32, 295 (1968). The hyperglycemic and hypoglycemic properties are demonstrated in the rat by a modification of the method described by Holland et al, in J. Med. Pharm. Chem. 3, 99 (1961) and by Barthelmai et al., in Klin. Wchschr. 40, 585 (1962).

When one of the compounds of formula (1) is employed as an anti-inflammatory, analgesic, hyperglycemic and/or hypoglycemic agent in warm-blooded animals, e.g. in mice or rats, it may be used alone or in combination with pharmaceutically-acceptable carriers, the proportion of which is determined by the solubility and chemical nature of the compound, chosen route of administration and standard biological practice. For example, an anti-inflammatory, analgesic, hyperglycemic and/or hypoglycemically effective amount of the compound may be administered orally in solid form containing such excipients as starch, sugar, certain types of clay and the like. Similarly, such an amount may also be administered in the form of solutions or suspensions, or the compound may be injected parenterally. For oral or parenteral administration, the compound may be used in the form of a sterile solution or suspension in a pharmaceutically-acceptable liquid carrier such as water, ethanol, propylene glycol, or polyethylene glycol, containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide), also e.g., "TWEEN 80" (registered trademark) and the like. The dosage of the present compounds of formula (1) will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford anti-inflammatory, analgesically, hyperglycemic and/or hypoglycemically effective results without causing any harmful or deleterious side effects and preferably at a level that is in a range of from about 1.0 mg to about 250 mg per kilo per day, although as aforementioned variations will occur. However, a dosage level that is in the range of from about 10 mg to about 100 mg per kilo per day is most desirably employed in order to achieve effective results.

The anti-inflammatory, analgesic, hyperglycemic and/or hypoglycemic activities of the compounds of this invention are well within the range of those of a number of well known drugs commonly used for the same purposes.

The following non-limitative examples illustrate some selected methods for producing the compounds according to the present invention, as well as comparative data illustrating the therapeutic effect of representative compounds according to the present invention.

EXAMPLE 1

N-(2-pyridylcarbonylamino-1-oxide)-1,2,3,6-tetrahydropyridine (A-36)

2,4-dinitrophenylpyridinium chloride I (1.82 g, 6.48 mmol) was dissolved in 30 ml of methanol and the solution cooled to 0° C. A suspension of picolinic acid hydrazide-1-oxide II (1.98 g, 12.95 mmol) in 40 ml of methanol was added to the cooled solution in five portions from an addition funnel with continuous stirring. Triethylamine (0.9 ml) was added and the reaction mixture stirred at room temperature for 12 hours. The solid which precipitated III was filtered off and washed with 60 ml each of methanol, water, methanol and ether in this order. This washed solid III was suspended in 150 ml of a dioxane-water mixture (4:1 ratio) and the suspension boiled under reflux for 12 hours to afford a clear solution. The solvent was evaporated under reduced pressure. Water (150 ml) was added to the residue and the insoluble material filtered off. Evaporation of the solvent from the filtrate above afforded N-(2-pyridylcarbonylimino-1-oxide) pyridinium ylide IV which can be purified further by elution from a 2.5×21 cm neutral alumina column using 250 ml ether-methanol (1:4 ratio) to give 0.295 g IV (21%) as a tan solid with mp 201°–204° C.

Sodium borohydride (50 mg) was added to 10 ml of 95% ethanol pre-cooled to 0° C. A solution of N-(2-pyridylcarbonylimino-1-oxide) pyridinium ylide IV (0.10 g., 0.47 mmol) in 30 ml of 95% ethanol was then added dropwise with continuous stirring. The reaction was maintained at 0° C. for 4 hours after which the reaction mixture was poured onto 25 g of crushed ice and allowed to stand at room temperature for 30 minutes. This solution was then extracted with chloroform (4×20 ml), the chloroform extract dried (Na$_2$SO$_4$) and filtered. The solvent was removed from the filtrate at reduced pressure to give 0.085 g (83%) of N-(2-pyridylcarbonylamino-1-oxide)-1,2,3,6-tetrahydropyridine V as a tan solid with mp 91°–93° C. The structure assigned to N-(2-pyridylcarbonylamino-1-oxide)-1,2,3,6-tetrahydropyridine was in agreement with its infrared (IR), mass spectral (MS) and nuclear magnetic resonance (NMR) spectra. Mass spectra (70 ev): Mass calculated for C$_{11}$H$_{13}$N$_3$O$_2$: 219.1008; Found: 219.1009.

EXAMPLE 2

Related N-(substituted-carbonylamino)-1,2,3,6-tetrahydropyridines have been prepared using equivalent quantities of other carbonylhydrazides using procedures similar to that outlined in the preceding example. The melting point for each product prepared is set out in Table 1.

TABLE 1

N-(substituted carbonylamino)-1,2,3,6-tetrahydropyridines (1) prepared according to Example 2

| Chemical Name | Designation | R$^1$ | R$^2$ | MP |
|---|---|---|---|---|
| N-(benzoylamino)-3(diethylaminocarbonyl)-1,2,3,6-tetrahydropyridine | A-43 | phenyl | —CONEt$_2$ | 35–37° |
| N-(3-picolylcarbonylamino)-1,2,3,6-tetrahydropyridine | A-48 | 3-pyridyl-CH$_2$— | H | 133–136° |
| N-(phenylethylcarbonylamino)-1,2,3,6-tetrahydropyridine | A-55 | phenyl-CH$_2$—CH$_2$— | H | 81–84° |
| N-(phenoxymethylenecarbonylamino)-1,2,3,6-tetrahydropyridine | A-62 | phenyl-O—CH$_2$— | H | 104–107° |
| N-(cyclohexylcarbonylamino)-1,2,3,6-tetrahydropyridine | A-63 | cyclohexyl | H | 155–158° |
| N-(3,4-methylenedioxyphenylmethylenecarbonylamino)-1,2,3,6-tetrahydropyridine | A-70 | 3,4-methylenedioxyphenyl-CH$_2$— | H | 134–136° |
| N-(4-methoxyphenylcarbonylamino)-1,2,3,6-tetrahydropyridine | A-77 | MeO-phenyl- | H | 149–151° |
| N-(4-methylphenylcarbonylamino)-1,2,3,6-tetrahydropyridine | A-78 | Me-phenyl- | H | 137–139° |
| N-(4-chlorophenylcarbonylamino)-1,2,3,6-tetrahydropyridine | A-79 | Cl-phenyl- | H | 160–162° |
| N-(3,4-dichlorophenylcarbonylamino)-1,2,3,6-tetrahydropyridine | A-80 | 3,4-dichlorophenyl- | H | 157–159° |

EXAMPLE 3

N-[4-(1-methoxycarbonyl-1,2-dihydropyridyl)carbonylamino]-1,2,3,6-tetrahydropyridine (A-45)

A solution of methyl chloroformate XII (0.202 g, 2.15 mmol) dissolved in methanol (20 ml) was added dropwise from an addition funnel to a solution of N-(4-pyridylcarbonylamino)-1,2,3,6-tetrahydropyridine XI (0.218 g, 1.07 mmol) in 20 ml methanol pre-cooled to −65° C. with stirring. The reaction was allowed to proceed for 30 minutes at −65° C. to yield N-[4-(1-methoxycarbonylpyridinium)carbonylamino]-1,2,3,6-tetrahydropyridine chloride XIII to which sodium borohydride (0.8 g) was added. The reaction was allowed to proceed for an additional 3 hours at −65° C. and then poured onto crushed ice (125 ml) followed by gradual warming to room temperature. This solution was then extracted with chloroform (4×50 ml), the chloroform extract was dried (Na$_2$SO$_4$) and filtered. Removal of the solvent from the filtrate in vacuo gave a white solid which was purified by elution from a 2.5×20 cm silica gel column using ether (400 ml) to afford 0.199 g (70.5%) N-[4-(1-methoxycarbonyl-1,2-dihydropyridyl)-carbonylamino]-1,2,3,6-tetrahydropyridine XIV as a white solid with mp 132°–134°. The structure assigned to N-[4-(1-methoxycarbonyl-1,2-dihydropyridyl)carbonylamino]-1,2,3,6-tetrahydropyridine is in agreement with its infrared (IR), mass spectral (MS) and nuclear magnetic resonance (NMR) spectra. Mass spectrum (70ev): mass calculated for C$_{13}$H$_{17}$N$_3$O$_3$: 263.1270; found: 263.1267.

EXAMPLE 4

N-[4-(1-methoxycarbonyl-1,2,3,6-tetrahydropyridyl)-carbonylamino]-1,2,3,6-tetrahydropyridine (A-49)

A solution of methyl chloroformate XII (0.38 g, 4.02 mmol) was added dropwise to a solution of N-(4-pyridylcarbonylamino)-1,2,3,6-tetrahydropyridine XI (0.40 g, 2.01 mmol) dissolved in 40 ml 95% ethanol precooled to −65° C. with continuous stirring. The reaction was allowed to proceed for 30 minutes at −65° C. with stirring to yield N-[4-(1-methoxycarbonylpyridinium)carbonylamino]-1,2,3,6-tetrahydropyridine chloride XIII to which sodium borohydride (0.25 g) was added. The reaction was allowed to proceed for 4 hours at 0° C. and then poured onto crushed ice (125 ml) followed by gradual warming to room temperature. This solution was extracted with chloroform (4×50 ml), the chloroform extract was dried (Na$_2$SO$_4$) and filtered. Removal of the solvent from the filtrate in vacuo gave a solid which was purified by elution from a 2.5×17 cm neutral alumina column using ethyl acetate (400 ml) to yield 0.281 g (53%) N-[4-(1-methoxycarbonyl-1,2,3,6-tetrahydropyridyl)carbonylamino]-1,2,3,6-tetrahydropyridine XV as a white solid with mp 153°–155° C. The structure assigned to N-[4-(1-methoxycarbonyl-1,2,3,6-tetrahydropyridyl)carbonylamino]-1,2,3,6-tetrahydropyridine is in agreement with its infrared (IR), mass spectral (MS) and nuclear magnetic resonance (NMR) spectra. Mass spectrum (70 ev): mass calculated for C$_{13}$H$_{19}$N$_3$O$_3$: 265.1426; found: 265.1429.

EXAMPLE 5

N-[4-(1-methyl-1,2,3,6-tetrahydropyridyl)carbonylamino]-1,2,3,6-tetrahydropyridine (A-50)

Methyl iodide XVI was added to a solution of N-(4-pyridylcarbonylamino)1,2,3,6-tetrahydropyridine XI (5.0 g, 24.6 mmol) dissolved in dry methylene chloride (120 ml). The reaction was allowed to proceed for 4 hours with stirring at 25° C. prior to heating at reflux for an additional 4 hours. The solvent was then removed in vacuo to afford a hygroscopic intense yellow solid which contained N-[4-(1-methylpyridinium)carbonylamino]-1,2,3,6-tetrahydropyridine iodide XVII. This yellow solid was then dissolved in 120 ml methanol and the solution was cooled to −65° C. Sodium borohydride (1.8 g) was added in one aliquot and the reaction was allowed to proceed for 4 hours at −65° C. The reaction mixture was then poured onto 125 ml crushed ice and allowed to warm to room temperature. This solution was extracted with chloroform (4×50 ml), the chloroform extract was dried ($Na_2SO_4$) and filtered. Removal of the solvent from the filtrate in vacuo gave a solid which was purified further by elution from a 2.5×18 cm neutral alumina column. Elution using 400 ml ether-methanol (10:1 v/v) afforded 1.289 g (23.7%) N-[4-(1-methyl-1,2,3,6-tetrahydropyridyl)carbonylamino]-1,2,3,6-tetrahydropyridine XVIII as a white solid with mp 119°–122° C. The structure assigned to N-[4-(1-methyl-1,2,3,6-tetrahydropyridyl)carbonylamino]-1,2,3,6-tetrahydropyridine is in agreement with its infrared (IR), mass spectral (MS) and nuclear magnetic resonance (NMR) spectra. Mass spectrum (70 ev): mass calculated for $C_{12}H_{19}N_3O$: 221.1529; found: 221.1529.

BIOLOGICAL TESTING

Initially the activity of the compound tested on an animal was determined at a single dose. If the substance was active at this dose, it was subjected to limited repeat testing. If the presence of activity was confirmed by repetition of the testing, a dose response relation was constructed and the effective dose ($ED_{50}$) determined. If toxicity was encountered with the initial dose, the dose was reduced until one was reached which was tolerated by the animals tested.

EXAMPLE 6

Analgesic Activity

Substances were administered subcutaneously to five Swiss albino mice, weighing 18 to 22 grams, before determining their activity in the phenylquinone-writhing test (see Collier et al, cited above). The active ingredients were suspended in a solution of physiological saline and "Tween 80 TM" surfactant. A dose amounting to 10 milliliters of physiological saline solution and active ingredient per kilogram of bodyweight was administered to the mice according to the dosage as set out in Table 2. The test results are shown in Table 2, the compounds tested being compared to Aspirin TM and dextropropoxyphene TM.

TABLE 2

Analgesic activity of N-(carbonylamino)-1,2,3,6-tetrahydropyridines tested

| Substance | Dose mg/kg | Response % inhibition | $ED_{50}$ mg/kg* | 95% confidence limits |
|---|---|---|---|---|
| A-36 | 128 | 55.3 | | |
| A-43 | 128 | 39.0 | | |
| A-45 | 16 | 61 | | |
|  | 32 | 61 | | |
|  | 128 | 97 | | |
|  | 256 | 95 | | |
| A-48 | 8 | 28 | | |
|  | 16 | 45 | | |
|  | 32 | 94 | 14.5 | |
|  | 128 | 100 | | |
|  | 256 | 100 | | |
| A-49 | 64 | 3 | | |
|  | 128 | 78 | | |
|  | 256 | 95 | | |
| A-50 | 256 | 47 | | |
| A-55 | 120 | 42 | | |
| A-62 | 25 | 50 | 25.0 | (16–40) |
| A-63 | 16.5 | 50 | 16.5 | (4–66) |
| A-70 | 60 | 80 | | |
|  | 120 | 91 | | |
| A-77 | 128 | 31.4 | | |
| A-78 | 64 | 92.4 | | |
| A-79 | 64 | 33.9 | | |
| A-80 | 128 | 72.0 | | |
| Standards: | | | | |
| Aspirin (TM) | | | 52 | (34.6–78.0) |
| Dextropropoxyphene (TM) | | | 56 | |

*Determined by the method Litchfield and Wilcoxon (J. Pharmacol. Exp. Therap. 96: 99, 1949).

Compounds A-45, A-48, A-49, A-62, A-63, A-70, A-78 and A-80 appears as active analgesics, comparing with the standard compounds aspirin TM and Dextropropoxyphene TM.

EXAMPLE 7

Anti-inflammatory Activity

Substances were administered subcutaneously to six Sprague-Dawley rats, weighing 100–120 g. A suspension of 0.03% carageenan was injected under the plantar skin of a hind paw. The increase in volume of the inflamed paw was measured 3 and 5 hours after drug administration. The percent of animals with significantly lower inflamed paw volumes than the untreated control animals was calculated (see C. A. Winter, cited above).

The test results are shown in Table 3.

TABLE 3

Anti-inflammatory activity of N-(carbonylamino)-1,2,3,6-tetrahydropyridine derivatives

| Substance | Dose mg/kg | Response % Inhibition 3 hrs. after drug | Response % Inhibition 5 hrs. after drug |
|---|---|---|---|
| A-36 | 128 | 34 | 0 |
| A-45 | 128 | 50 | 83 |
| A-48 | 128 | 50 | 50 |
| A-49 | 128 | 0 | 50 |
| A-55 | 120 | 83 | 83 |
| A-62 | 120 | 83 | 80 |
| A-63 | 120 | 50 | 84 |
| Standard: | | | |
| Indomethacin (Trademark) | 32 | 17 | 83 |

A-45, A-48, A-55, A-62 and A-63 show a striking anti-inflammatory action, comparing favourably with the standard compound used.

EXAMPLE 8

Determination of Blood Glucose

Compounds were suspended in distilled water and were administered orally to overnight-fasted Wistar rats. Capillary blood samples were obtained from the tail at zero, two, and four hours post-treatment and the sera derived from these samples were analyzed for glucose by spectrophotometric determination of enzymatically produced $NADH_2$ (reduced form of nicotinamide adenine dinucleotide), using the commercial reagent "Escalab G-15 ™" according to the method described by Holland et al and by Barthelmai et al, both cited above. The test results are shown in Tables 4 and 5, and the $ED_{50}$ values shown in Table 4 were calculated as the dose of compound which elevated blood glucose levels by 50 percent.

TABLE 4

Hyperglycemic Activity of Compounds Tested

| Substance | % change in blood-glucose concentration Post-Treatment | | | |
|---|---|---|---|---|
| | $ED_{50}$* mg/kg 2 hours | 95% confidence limits | $ED_{50}$* mg/kg 4 hours | 95% confidence limits |
| A-62 | 41 | (22–76) | 53 | (30–93) |
| A-63 | 36.5 | (15–91) | 53 | (19–148) |

*Determined by the method of Litchfield and Wilcoxon (J. Pharmacol. Exp. Therap. 96: 99, 1949)

A-62 and A-63 demonstrate significant hyperglycemic activity in this test.

TABLE 5

Hypoglycemic Activity of Compounds Tested

| Substance | Dose mg/kg | % change in blood-glucose concentrations Post-Treatment | |
|---|---|---|---|
| | | 2 hours | 4 hours |
| A-77 | 100 | −69 | −26 |
| A-78 | 100 | −73 | −41 |
| A-79 | 100 | −109 | −26 |
| A-80 | 100 | −50 | −50 |
| Standard: Chlorpropamide (TM) | 100 | > −40 | > −40 |

A-77, A-78, A-79, and A-80 exhibit potent hypoglycemic activity.

We claim:

1. A compound of the formula and their non-toxic pharmaceutically-acceptable salts, wherein $R^1$ is selected from cycloalkyl having 3–7 carbon atoms, aralkyl having 1–6 carbon atoms in the alkyl group, phenoxyalkyl having 1–6 carbon atoms in the alkyl group, phenyl when $R^2$ is $CONH_2$ or $CON$ (lower alkyl)$_2$, and phenyl substituted by halogen, by $NH_2$, by OH, by COOH, by $CONH_2$ or by CON (lower alkyl)$_2$;

and $R^2$ is selected from hydrogen, $NH_2$, OH, halogen, COOH, $CONH_2$ and CON (lower alkyl)$_2$.

2. A N-(Carbonylamino)-1,2,3,6-tetrahydropyridine as claimed in claim 1 wherein $R^2$ is hydrogen or diethylaminocarbonyl; and $R^1$ is a substituent selected from the group consisting of phenyl, phenylethyl, phenoxymethylene, cyclohexyl, 3,4-methylenedioxyphenylmethylene, chlorophenyl and dichlorophenyl, with the proviso that $R^2$ is diethylaminocarbonyl when $R^1$ is phenyl.

3. N-(benzoylamino)-3-(diethylaminocarbonyl)-1,2,3,6-tetrahydropyridine as claimed in claim 1.

4. N-(phenylethylcarbonylamino)-1,2,3,6-tetrahydropyridine as claimed in claim 1.

5. N-(phenoxymethylenecarbonylamino)-1,2,3,6-tetrahydropyridine as claimed in claim 1.

6. N-(cyclohexylcarbonylamino)-1,2,3,6-tetrahydropyridine as claimed in claim 1.

7. N-(4-chlorophenylcarbonylamino)-1,2,3,6-tetrahydropyridine as claimed in claim 1.

8. N-(3,4-dichlorophenylcarbonylamino)-1,2,3,6-tetrahydropyridine as claimed in claim 1.

9. N-(3,4-methylenedioxyphenylmethylenecarbonylamino)-1,2,3,6-tetrahydropyridine as claimed in claim 2.

* * * * *